United States Patent [19]

Mueller

[11] Patent Number: 4,671,328
[45] Date of Patent: Jun. 9, 1987

[54] DISPENSING CLOSURE FOR CHEMICAL AND PHARMACEUTICAL SUBSTANCES, AND METHOD OF MANUFACTURING SAME

[75] Inventor: Klaus F. Mueller, Dreieich, Fed. Rep. of Germany

[73] Assignee: Firma Klaus F. Mueller Pharmaverkaufsbuero, Fed. Rep. of Germany

[21] Appl. No.: 842,246

[22] Filed: Mar. 21, 1986

[30] Foreign Application Priority Data

Mar. 21, 1985 [DE] Fed. Rep. of Germany ....... 3510166

[51] Int. Cl.$^4$ ................................................ B65B 1/04
[52] U.S. Cl. ........................................ 141/1; 141/309; 222/479; 222/527
[58] Field of Search ............................. 141/1–2, 141/18, 285, 311 R, 309, 386, 389, 345, 366; 604/414; 222/478–479, 526–527, 566

[56] References Cited

U.S. PATENT DOCUMENTS

| 2,847,042 | 8/1958 | Edelmann | 222/479 X |
| 3,193,143 | 7/1965 | Maieli | 222/478 X |
| 3,885,607 | 5/1975 | Peltier | 141/329 |
| 4,475,914 | 10/1984 | Portnoff | 604/414 |
| 4,559,983 | 12/1985 | Paoletti | 141/260 |
| 4,573,506 | 3/1986 | Paoletti | 141/98 |
| 4,589,879 | 5/1986 | Pearson | 604/411 |

FOREIGN PATENT DOCUMENTS 155298 2/1954 Australia ............................. 222/478

*Primary Examiner*—Joseph J. Rolla
*Assistant Examiner*—Michael S. Huppert
*Attorney, Agent, or Firm*—Robert J. Koch

[57] ABSTRACT

A dispensing closure for chemical and pharmaceutical substances, particularly narcotic liquids, narcotic gases, or the like, the closure comprised of a sealing cap (1) which is to be applied to the opening of the substance-dispensing container, and further comprised of an adapter piece (2) with code markings (3), to establish a joint between the adapter and a receiving structure on the container being filled, which receiving structure has corresponding markings, wherewith the sealing cap (1) and the adapter (2) are interconnected by a flexible, liquid-passing tube (6) which opens into a transverse bore hole passage (9) for liquid, and by a flexible air-delivery tube (8) which opens into a transverse air admission bore hole (10). The adapter piece (2), the flexible, liquid-passing tube (6), and the sealing cap (1) are comprised of a single piece having a longitudinal bore (11) passing through its entire length, wherewith the opening of said bore at the adapter end of the bore is sealed off with a sealing stopper (13) having a blind hole (12) into which the flexible air-delivery tube (8) extends, wherewith the air-delivery tube (8) is held in place in the blind hole. Air-delivery tube (8) communicates with the atmosphere via a transverse bore hole (10) which passes through the adapter piece (2), the sealing stopper (13), and the wall of the air-delivery tube (8). The flexible, liquid-passing tube (6) is provided with a corrugation (14).

4 Claims, 1 Drawing Figure

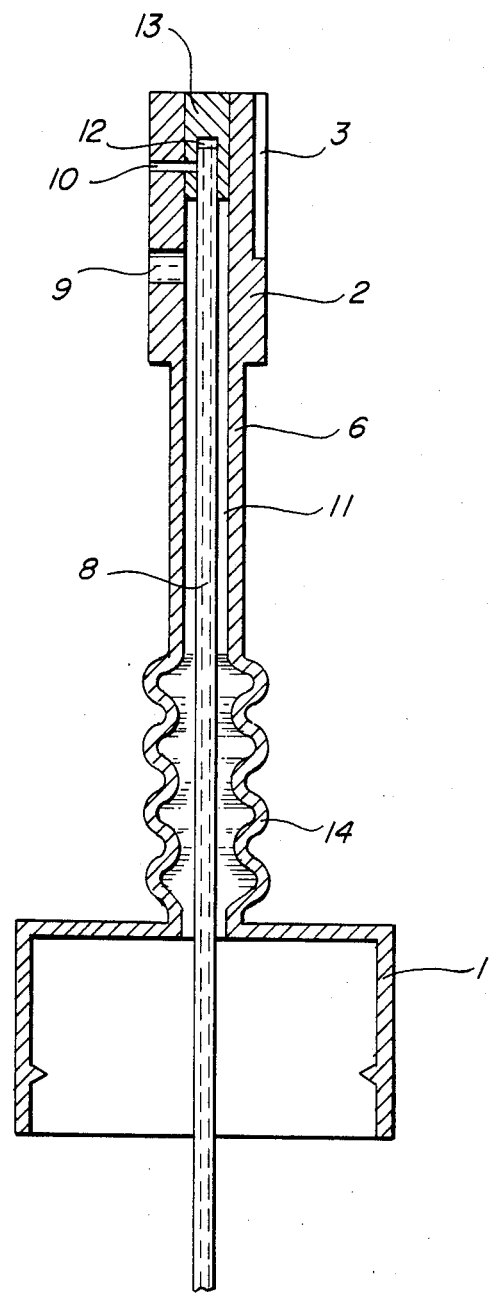

DISPENSING CLOSURE FOR CHEMICAL AND PHARMACEUTICAL SUBSTANCES, AND METHOD OF MANUFACTURING SAME

BACKGROUND OF THE INVENTION

1. Field of the Invention

The invention relates to a dispensing closure for chemical and pharmaceutical substances, particularly narcotic liquids, narcotic gases, or the like, said closure comprising a sealing or closure cap which is applied to the opening of the substance-dispensing container, and further comprising of an adapter piece with code markings, to establish a joint between the adapter and a receiving structure on the container being filled. The receiving structure has corresponding markings. The sealing cap and the adapter are interconnected by a flexible, liquid-passing tube which opens into a transverse bore hole passage for liquid, and by a flexible air-delivery tube which opens into a transverse air admission bore hole.

2. Description of the Related Art

In a known dispensing closure, the sealing cap and the adapter piece are each provided with a tube nipple over which a piece of flexible tubing is pushed. This flexible tubing is secured to each of the nipples by a respective ring clamp to prevent it from being pulled off. The adapter piece is provided with a blind hole, and with two transverse holes of different diameters which extend into the blind hole. The larger diameter transverse hole serves as a liquid passage, and the smaller diameter transverse hole serves to hold the flexible ventilation tube in place, which tube extends through the entire length of the dispensing closure and is pulled into the smaller transverse hole by bending said tube around. The known dispensing closure is very costly to manufacture and assemble. It has at least six parts, some of which are metal and some plastic. It is costly to assembly because one must push the ends of the flexible tubing over the tube nipples, apply the ring clamps, and laboriously install or "thread-in" the flexible air-delivery tube, all separate, labor-intensive steps. In particular, there are substantial problems presented in passing the air-delivery tube around the 90° bend inside the narrow liquid passage.

SUMMARY OF THE INVENTION

The underlying problem of the invention is to devise a dispensing closure of the type described supra, which is simple and easy to manufacture, assemble and install. The invention comprises the following: the adapter piece, the flexible, liquid-passing tube, and the sealing cap are comprised of a single piece having a longitudinal bore passing through its entire length, wherewith the opening of said bore at the adapter end of said bore is sealed off with a sealing stopper which is provided with a blind hole into which the flexible air-delivery tube extends, wherewith said air-delivery tube is held in place in said blind hole and communicates with the atmosphere via a transverse bore hole which passes through the adapter piece, the sealing stopper, and the wall of the said flexible air-delivery tube.

The invention affords a dispensing closure which is simple and easy to manufacture, assemble and install with only three pieces, all of which are pre-manufactured from thermoplastic material, and said pieces are assembled by simple plug and/or adhesive joints, with the final phase of manufacture comprising merely the production of two transverse bore holes, in a single machining step. There are none of the highly material- and labor-consuming procedures involved in the application of ring clamps or the like, or in threading-in the flexible air-delivery tube.

In another embodiment of the invention, advantageously the flexible, liquid-passing tube is provided with a corrugation or corrugated tube wall, thus conferring a high degree of flexibility on the dispensing closure, whereby vessels can be filled while disposed at substantial angles from the dispensing container.

According to the invention. the dispensing closure is manufactured as follows: the adapter piece, the flexible, liquid-passing tube, and the sealing cap are produced from a single piece with a longitudinal bore extending through the entire length. The flexible air delivery tube is inserted into the blind hole of the sealing stopper, and the stopper is inserted into the longitudinal bore such that the flexible air-delivery tube extends through the dispensing closure inside the liquid tube. Then the two transverse passages are produced in the adapter, with one of these to serve as a liquid passage from the exterior of the sealing stopper to the longitudinal bore, and the other to serve as an air admission passage from the environs of the sealing stopper to the interior of the flexible air-delivery tube.

BRIEF DESCRIPTION OF THE DRAWING

An exemplary embodiment of the inventive dispensing closure is illustrated in longitudinal cross section in the FIGURE.

DETAILED DESCRIPTION OF THE PREFERRED EMBODIMENT

The dispensing closure illustrated in the FIGURE is comprised of a sealing cap 1 which is to be applied to the opening of the substance-dispensing container, and is further comprised of an adapter piece 2 with a code marking 3, to establish a joint or connection between the adapter and a receiving structure on the container being filled, which receiving structure has a corresponding marking. The sealing cap 1 and the adapter piece 2 are interconnected by means of a flexible, liquid-passing tube 6 and a flexible air-delivery tube 8 which tube 8 extends through the entire dispensing closure and which extends into the liquid-dispensing container when the dispensing closure is installed. The adapter piece is provided with a transverse liquid passage 9 and a transverse air admission passage 10. The adapter piece 2, the flexible, liquid-passing tube 6, and the sealing cap 1 are comprised of a single piece through which a longitudinal bore 11 extends from end to end. The opening of bore 11 at the adapter end of said bore is sealed off with a sealing stopper 13 which is provided with a blind hole 12 into which the flexible air-delivery tube 8 extends, wherewith tube 8 is held in place in hole 12. Tube 8 communicates with the atmosphere via a transverse air admission passage 7 which passes through the adapter piece 2, the sealing stopper 13, and the wall of tube 8. The flexible, liquid-passing tube 6 is provided with a corrugated wall 14 which confers greatly improved flexibility on the dispensing closure.

The dispensing closure is manufactured according to the invention as follows: the adapter piece 2, the flexible, liquid-passing tube 6, and the sealing cap 1 are produced from a single piece with a longitudinal bore 11 extending through the entire length. The flexible air-delivery tube 8 is inserted into the blind hole 12 of the sealing stopper 13, and stopper 13 is inserted into bore 11 such that air tube 8 extends through the dispensing closure inside the liquid tube 6. Then the two transverse passages 9 and 10 are produced in the adapter 2, with passage 9 to serve as a liquid passage from the exterior of the sealing stopper 13 to longitudinal bore 11, and passage 10 to serve as an air admission passage from the environs of the sealing stopper 13 to the interior of the flexible air-delivery tube 8.

I claim:

1. A dispensing closure for chemical and pharmaceutical substances, particularly narcotic liquids, narcotic gases, or the like, said closure comprised of a sealing cap which is to be applied to the opening of the substance-dispensing container, and further comprised of an adapter piece with code markings, to establish a joint between the adapter and a receiving structure on the container being filled, which receiving structure has corresponding markings, wherewith the sealing cap and the adapter are interconnected by a flexible, liquid-passing tube which is in communication with a transverse bore hole passage for liquid passing through said adapter piece, and by a flexible air-delivery tube which opens into a transverse air admission bore hole; characterized in that the adapter piece (2), the flexible, liquid-passing tube (6), and the sealing cap (1) are comprised of a single piece having a longitudinal bore (11) passing through its entire length, wherewith the opening of said bore at the adapter end of said bore is sealed off with a sealing stopper (13) which is provided with a blind hole (12) into which the flexible air-delivery tube (8) extends, wherewith said air-delivery tube (8) is held in place in said blind hole and communicates with the atmosphere via said transverse air admission bore hole (10) which passes through the adapter piece (2), the sealing stopper (13), and the wall of said air-delivery tube (8).

2. A dispensing closure according to claim 1, characterized in that the flexible, liquid-passing tube (6) is provided with a corrugation (14).

3. A method of manufacturing a dispensing closure for chemical and pharmaceutical substances, particularly narcotic liquids, narcotic gases, or the like, according to claim 1; characterized in that the adapter piece (2), the flexible, liquid-passing tube (6), and the sealing cap (1) are produced from a single piece with the longitudinal bore (11) extending through the entire length, the flexible air-delivery tube (8) is inserted into the blind hole (12) of the sealing stopper (13), and the stopper (13) is inserted into said longitudinal bore (11) such that said air tube (8) extends through the dispensing closure inside the liquid tube (6), and then the two transverse passages (9, 10) are produced in the adapter piece (2), with one of said passages (9) to serve as a liquid passage from the exterior of the sealing stopper (13) to said longitudinal bore (11), and the other of said passages (10) to serve as an air admission passage from the environs of the sealing stopper (13) to the interior of the flexible air-delivery tube (8).

4. A method of manufacturing a dispensing closure for chemical and pharmaceutical substances, particularly narcotic liquids, narcotic gases, or the like, according to claim 2; characterized in that the adapter piece (2), the flexible, liquid-passing tube (6), and the sealing cap (1) are produced from a single piece with the longitudinal bore (11) extending through the entire length, the flexible air-delivery tube (8) is inserted, into the blind hole (12) of the sealing stopper (13), and the stopper (13) is inserted into said longitudinal bore (11) such that said air tube (8) extends through the dispensing closure inside the liquid tube (6), and then the two transverse passages (9, 10) are produced in the adapter piece (2), with one of said passages (9) to serve as a liquid passage from the exterior of the sealing stopper (13) to said longitudinal bore (11), and the other of said passages (10) to serve as an air admission passage from the environs of the sealing stopper (13) to the interior of the flexible air-delivery tube (8).

* * * * *